United States Patent [19]

Kleinschroth et al.

[11] Patent Number: 4,681,882

[45] Date of Patent: Jul. 21, 1987

[54] 4-ALKOXY-PYRIDO[2,3-D]PYRIMIDINE DERIVATIVES

[75] Inventors: Jörgen Kleinschroth; Gerhard Satzinger, both of Denzlingen; Karl Mannhardt, Elzach-Oberprechtal; Johannes Hartenstein, Stegen-Wittental; Hartmut Osswald, Waldkirch; Günter Weinheimer, Denzlingen; Edgar Fritschi, St. Peter, all of Fed. Rep. of Germany

[73] Assignee: Gödecke Aktiengesellschaft, Berlin, Fed. Rep. of Germany

[21] Appl. No.: 787,844

[22] Filed: Oct. 16, 1985

[30] Foreign Application Priority Data

Oct. 19, 1984 [DE] Fed. Rep. of Germany ....... 3438351

[51] Int. Cl.$^4$ .................. A61K 31/435; C07D 471/04
[52] U.S. Cl. ..................................... 514/258; 544/279
[58] Field of Search ......................... 544/279; 514/258

[56] References Cited

U.S. PATENT DOCUMENTS 4,361,700 11/1982 Purcell et al. ...................... 544/279
4,560,753 12/1985 Lesher et al. ...................... 544/279

OTHER PUBLICATIONS

Gorlitzer et al., *Arch. Pharm. (Weinheim)* vol. 314, pp. 938–949 (1981).

*Primary Examiner*—Donald G. Daus
*Assistant Examiner*—Barbara Cassatt
*Attorney, Agent, or Firm*—Elizabeth M. Anderson

[57] ABSTRACT

4-Alkoxy-pyrido[2,3-d]pyrimidine derivatives are described as well as processes for their preparation.

For reason of their vasospasmolytic effects these compounds are mainly indicated for the treatment of cerebral, cardiac, and peripheral vascular diseases such as myocardiac ischemia, cerebral infarction, pulmonary thromboses, as well as in cases of arteriosclerosis and other stenotic disorders. They are therefore valuable agents for combating cardiovascular mortality.

9 Claims, No Drawings

4-ALKOXY-PYRIDO[2,3-D]PYRIMIDINE DERIVATIVES

SUMMARY OF THE INVENTION

The invention concerns new 4-alkoxy-pyrido[2,3-d]pyrimidine derivatives of the general Formula I

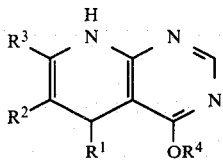

wherein
- $R^1$ represents an unsubstituted or substituted aromatic or heteroaromatic ring;
- $R^2$ represents a nitrile group, a carboxyl group or an alkoxycarbonyl residue with up to six carbon atoms;
- $R^3$ is a straight-chained or branched alkyl group with up to four carbon atoms or an amino group; and
- $R^4$ represents a straight-chained or branched alkyl group with up to four carbon atoms; as well as optionally the pharmaceutically acceptable salts thereof.

Another subject matter of the present invention is the use of 4-alkoxy-pyrido[2,3]pyrimidine derivatives of the general Formula I for the treatment of vascular diseases and pharmaceutical compositions containing the new compounds.

DETAILED DESCRIPTION

The compounds of the present invention may be prepared by a process characterized in that 4-oxopyrido[2,3-d]pyrimidine derivatives of the general Formula III.

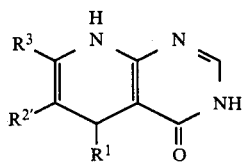

wherein $R^1$ and $R^3$ have the above meaning, and $R^{2'}$ represents a nitrile group or an alkoxycarbonyl residue with up to six carbon atoms, is O-alkylated in a generally known manner.

The compounds of the general Formula III serving as the starting products are prepared by either:

(a) reacting a dihydropyridine of the general Formula IV

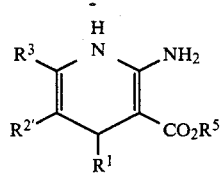

wherein $R^1$, $R^{2'}$, $R^3$, and $R^5$ have the above meaning, with s-triazine in the presence of a base, or (b) condensing a compound of the general Formula V

wherein $R^1$ and $R^{2'}$ have the above meaning, and $R^{3'}$ represents a straight-chained or branched alkyl group with up to four carbon atoms, by heating in a polar solvent with 6-amino-4-hydroxypyrimidine.

Compounds of the general Formula I, in which $R^2$ represents a carboxyl group, are prepared by hydrolyzing compounds of the general Formula I, in which $R^2$ represents an alkoxycarbonyl residue suitable for the splitting of esters, in a generally known manner, preferably in an acid medium.

The compounds of the general Formula IV (cf. e.g., "Liebig's Ann. Chem." 1977, p. 1895, or "Arzneim. Forsch." 31 (II), 8 (1981), p. 1173) and V (cf. e.g., "Arch. Pharm." 317 (1984), p 709) are known from the literature and can be prepared in an analogous manner.

In order to perform reaction (a) the dihydropyridine derivative is heated to temperatures between 50° and 160° C., preferably 100°–150° C., together with s-triazine in an inert organic solvent in the presence of strong bases such as, e.g., alkali alcoholates or sodium hydride in an inert organic solvent. Suitable solvents are mainly polar solvents such as dimethylsulfoxide, dimethylformamide or ethyleneglycol dimethylether.

This reaction produces, in addition to the compounds of the general Formula III isolated as the main products, also compounds according to German Offenlegungschrift No. 33 27 650, which are separated by chromatography.

The reaction (b) is performed by heating the two components in an acid medium, preferably in boiling glacial acetic acid.

Pursuant to the invention the 4-alkoxy-pyrido[2,3-d]pyrimidine derivatives of the general Formula I are prepared according to the usual processes as described for the O-alkylation of lactams in the literature (cf. "Adv. Heterocyclic Chem." 12 (1970), 185–212). Suitable alkylation agents are alkyl halides and alkyl sulfonates, dialkyl sulfates and trialkyl oxonium salts.

For the reaction with alkyl halides the compounds of the general Formula III are used in the form of their metallic salts, preferably their alkali salts or silver salts, which are either prepared separately or in situ by means of suitable bases such as metallic hydrides, carbonates or alkoxides in an aprotic solvent. Dependent on the alkylation agent used suitable solvents are almost all inert organic solvents such as open-chained, cyclic or aromatic hydrocarbons, e.g., n-pentane, n-hexane, cyclohexane, benzene, or toluene, halogenated hydrocarbons such as dichloromethane and 1,2-dichloroethane, ether, such as, e.g., diethylether and 1,2-dimethoxyethane, as well as dipolar aprotic solvents such as dimethylformamide, hexamethylphosphoric acid triamide and dimethylsulfoxide. Dependent on the solvent used the temperature may vary between −20° C. and the boiling point of the respective solvent.

For reason of the ambident character of the lactam anion, and dependent on the reaction conditions and alkylation agents used, the alkylation often yields mixtures of O-alkylation and N-alkylation products ("J. Org. Chem." 32 (1967), 4040 ff).

The product mixtures thus obtained may be separated by means of chromatography and/or crystallization.

The 4-alkoxy-pyrido[2,3-d]pyrimidine derivatives of the general Formula I are obtained preferably by reacting the 4-oxo-pyrido[2,3-d]pyrimidines of the general Formula III with trialkyl oxonium salts, in particular trimethyloxoniumtetrafluoroborate, in an aprotic solvent. The O-isopropyl compounds, on the other hand, are advantageously obtained by alkylation of the alkali metallic salts with isopropyl halides.

Since the compounds of the general Formula I according to the invention have a chiral center at C-5 they may be present either as racemic mixtures, or in the form of the enantiomers.

The pharmaceutically acceptable salts are obtained in the usual manner by neutralization of the bases with corresponding inorganic or organic acids. As acids may be used, e.g., hydrochloric acid, sulfuric acid, phosphoric acid, lactic acid, citric acid, malic acid, salicyclic acid, ascorbic acid, malonic acid, or succinic acid.

By unsubstituted or substituted aromatic or heteroaromatic ring, there is meant phenyl or phenyl substituted by up to three of the same or different groups selected from a straight or branched alkyl with up to four carbon atoms, halogen selected from fluorine, chlorine, bromine or iodine, nitro, a straight or branched alkoxy with up to four carbon atoms, difluoromethoxy, trifluoromethoxy, dialkylamino in which alkyl is as defined above, alkylthio in which alkyl is as defined above or trifluoromethyl, or a methylenedioxy group; or a pyridyl, e.g., 2-, 3-, or 4-pyridyl, or thienyl group (2- or 3-) which is unsubstituted or substituted by alkyl as defined above.

Preferred are compounds of the general Formula I wherein:

$R^1$ represents an unsubstituted or substituted phenyl residue substituted, preferably in two or three position, by halogen, nitro, methyl, methoxy, difluoromethoxy, trifluoromethoxy, dimethylamino or diethylamino, methylthio or trifluoromethyl, or a phenyl residue disubstituted, preferably in 2,3 position by methoxy or methylenedioxy, or in 2,3 or 2,6 position by halogen atoms, which may be the same or different;

$R^2$ represents a nitrile group, a carboxyl group or an alkoxycarbonyl residue, in particular a methoxy, ethoxy, isopropoxy, isobutoxy, or methoxyethoxy carbonyl residue;

$R^3$ represents a methyl or ethyl residue or an amino group;

$R^4$ represents a methyl, ethyl, n-propyl or isopropyl residue.

The compounds of the general Formula I possess valuable pharmacological properties. In particular they produce calcium-antagonistic effects such as, e.g., termination of smooth-muscle contraction from potassium depolarization induced by calcium.

For reason of their vasospasmolytic effects the compounds are mainly indicated for the treatment of cerebral, cardiac, and peripheral vascular diseases such as myocardiac ischemia, cerebral infarction, pulmonary thromboses, as well as in cases of arteriosclerosis and other stenotic disorders. The 4-alkoxypyrido[2,3-d]pyrimidine derivatives of the present invention are therefore valuable agents for combating cardiovascular mortality. Another subject-matter of the present invention is therefore the use of 4-alkoxypyrido[2,3-d]pyrimidine derivatives of the general Formula I in the treatment of vascular diseases.

The compounds of the general Formula II according to the invention may be applied in liquid or solid form, orally or parenterally. For the solution for injection mainly water is used containing such additives as stabilizers, solubilizers or buffers as are usual for solutions for injection.

Such additives are, e.g., tartrate and citrate buffers, ethanol, complex formers (such as ethylenediamine-tetraacetic acid and the nontoxic salts thereof) as well as high molecular weight polymers (such as liquid polyethylene oxide) to regulate viscosity. Solid vehicles are, e.g., starch, lactose, mannitol, methyl cellulose, talcum, highly dispersed silicic acid, high molecular weight fatty acids (such as stearic acid), gelatin, agar-agar, calcium phosphate, magnesium stearate, animal and vegetable fats, solid high molecular weight polymers (such as polyethylene glycol); if desired preparations for oral application may in addition contain flavors and/or sweetening agents.

The enterally administered single doses are in the order from about 5 to 250 mg, preferably 10–100 mg. Doses for parenteral application would be in the order from about 1 to 20 mg.

The following examples serve to illustrate the invention further.

EXAMPLE 1

(±)-5,8-Dihydro-4-isopropoxy-7-methyl-5-phenyl-pyrido[2,3-d]-pyrimidine-6-carboxylic acid ethyl ester To a stirred suspension of 1.0 g (34 mmol) sodium hydride (80% in liquid paraffin) in 60 ml dimethylformamide is added dropwise a solution of 6.5 g (21 mmol) (±)-3,4,5,8-tetrahydro-7-methyl-4-oxo-5-phenyl-pyrido[2,3-d]pyrimidine-6-carboxylic acid ethyl ester in 60 ml dimethylformamide. When the gas generation diminishes stirring is continued at room temperature for 30 minutes; subsequently 5.1 g (30 mmol) isopropyl iodide in 15 ml dimethyl formamide are added dropwise.

Stirring is continued at room temperature for 20 hours, the solvent evaporated under vacuum, and the residue mixed with 100 ml water by stirring. The crystals forming are filtered off, dried, dissolved in acetic acid ethyl ester, and subjected to chromatography on silica gel with toluene/acetic acid ethyl ester 1:1.

The fraction of the $R_f 0.5$ is isolated and recrystallized from diisopropylether/ethanol. This process yields (±)-5,8-dihydro-4-isopropoxy-7-methyl-5-phenyl-pyrido[2,3-d]pyrimidine-6-carboxylic acid ethyl ester in the form of colorless crystals with a mp of 201°–202° C.

The (±)-3,4,5,8-tetrahydro-7-methyl-4-oxo-5-phenyl-pyrido[2,3-d]pyrimidine-6-carboxylic acid ethyl ester used as the starting material is prepared as follows:

(±)-3,4,5,8-Tetrahydro-7-methyl-4-oxo-5-phenyl-pyrido[2,3-d]pyrimidine-6-carboxylic acid ethyl ester (process a)

To a stirred suspension of 4.5 g (150 mmol) sodium hydride (80% in liquid paraffin) in 75 ml dimethylformamide is added dropwise, and in nitrogen atmosphere, a solution of 40.6 g (123 mmol) (±)-2-amino-1,4-dihydro-6-methyl-4-phenylpyridine-3,5-dicarboxylic acid diethyl ester in 200 ml dimethylformamide. When the gas generation diminishes stirring is continued at room temperature for 30 minutes; subsequently 10.0 g (123 mmol)

s-triazine in 250 ml dimethylformamide are added dropwise. The reaction mixture is heated to 110° C. for 16 hours and reduced under vacuum when cool. The dark residue is subjected to chromatography on silica gel with dichloromethane/ethanol 95:5. The fraction of the $R_f 0.5$ is isolated, heated to boiling with acetone, and the crystals precipitated after cooling are recrystallized from ethanol for the purpose of further purification.

This process yields (±)-3,4,5,8-tetrahydro-7-methyl-4-oxo-5-phenyl-pyrido[2,3-d]pyrimidine-6-carboxylic acid ethyl ester in the form of beige crystals with a m.p. of 303°–305° C. (decomposition).

Analogously the following compounds are obtained.

(±)-5-(2-Fluorophenyl)-5,8-dihydro-4-isopropoxy-7-methyl-pyrido[2,3-d]pyrimidine-6-carboxylic acid ethyl ester (1.a)

m.p. 186°–187° C. from diisopropyl ether/ethanol.

(±)-5,8-Dihydro-4-isopropoxy-7-methyl-5-(3-nitrophenyl)pyrido[2,3-d]pyrimidine-6-carboxylic acid(2-methoxy)ethyl ester (1.b)

m.p. 170°–172° C. from diisopropyl ether/isopropanol.

(±)-5,8-Dihydro-4-isopropoxy-7-methyl-5-(2-trifluromethylphenyl)pyrido[2,3-d]pyrimidine-6-carboxylic acid methyl ester (1.c)

m.p. 214°–215° C. from diisopropyl ether/methanol.

(±)-5,8)Dihydro-4-isopropoxy-7-methyl-5-(3-nitrophenyl)pyrido[2,3-d]pyrimidine-6-carboxylic acid isopropyl ester (1.d)

m.p. 181°–182° C. from diisopropyl ether/isopropanol.

(±)-7-Amino-5,8-dihydro-4-isopropoxy-5-(2-methoxyphenyl)pyrido[2,3-d]pyrimidine-6-carboxylic acid ethyl ester (1.e)

m.p. 222°–223° C. from diisopropyl ether/acetic acid ethyl ester.

(±)-5,8-Dihydro-4-isopropoxy-7-methyl-5-(2-trifluoromethylphenyl)pyrido[2,3-d]pyrimidine-6-carboxylic acid ethyl ester (1.f)

m.p. 155° C. from diisopropyl ether.

(±)-5,8-Dihydro-4-isopropoxy-7-methyl-5-(3-nitrophenyl)pyrido[2,3-d]pyrimidine-6-carboxylic acid methyl ester (1.g)

m.p. 218°–219° C. from diisopropyl ether/methanol.

EXAMPLE 2

(±)-5,8-Dihydro-4-methoxy-7-methyl-5-(3-nitrophenyl)pyrido[2,3-d]pyrimidine-6-carboxylic acid isopropyl ester Three and 0.7 g (10 mmol) (±)-3,4,5,8-tetrahydro-7-methyl-5-(3-nitrophenyl)-4-oxo-pyrido[2,3-d]-pyrimidine-6-carboxylic acid isopropyl ester and 3.0 g (20 mmol) trimethyloxonium-tetrafluoroborate are stirred in 150 ml 1,2-dichloroethane in nitrogen atmosphere and at room temperature for three hours. The product is extracted twice with 50 ml saturated sodium hydrogen carbonate solution, the organic phase is separated, dried over sodium sulfate and reduced under vacuum. Twice recrystallizing the residue from diisopropyl ether/isopropanol yields the product in the form of colorless crystals with a mp of 212°–213° C.

The following comparison studies with isolated muscles serve to illustrate the pharmacological efficacy of the compounds according to the general Formula 1.

Isolated Smooth Muscles (Table 1)

Of rabbits (vessel ring segments of arteria basilaris and a. coronaria are mounted in an organ bath in a way to allow the measurement of isometric contractions. Contractile activity is elicited by a potassium depolarization in Tyrode's solution. This experimental set-up is a well-known standard model for the identification of substances blocking the calcium channels opened during the potassium depolarization (Fleckenstein, Calcium Antagonism in Heart and Smooth Muscle, J. Wiley & Sons, 1983).

TABLE 1

Concentrations ($IC_{50}$, mol/l) of compounds effecting a semimaximal inhibition of the $K^+$-depolarization contraction of vessel rings in the organ bath. A. bas. = arteria basilaris, a cor. = arteria coronaria of the rabbit; mean diameter 0.5–1.0 mm.

| Example Number | a. basilaris | a. coronaria |
|---|---|---|
| 1b | $3.9 \times 10^{-8}$ | $3.4 \times 10^{-8}$ |
| 1c | $4 \times 10^{-8}$ | $4.5 \times 10^{-8}$ |
| 1d | $3.3 \times 10^{-8}$ | $1.6 \times 10^{-7}$ |
| 1e | $2.8 \times 10^{-6}$ | $7.3 \times 10^{-8}$ |
| 1f | $3.8 \times 10^{-8}$ | $3.4 \times 10^{-8}$ |
| 1g | $2.8 \times 10^{-8}$ | $2.3 \times 10^{-7}$ |
| 2 | $2.5 \times 10^{-9}$ | $1.4 \times 10^{-7}$ |

We claim:
1. A compound of the formula

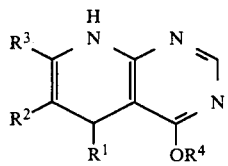

wherein
$R^1$ is phenyl, pyridyl or thienyl, or phenyl substituted by up to three of the same or different groups selected from a straight or branched alkyl with up to four carbon atoms, halogen, nitro, a straight or branched alkoxy with up to four carbon atoms, difluoromethoxy, trifluoromethoxy, dialkylamino, alkylthio or trifluoromethyl or a methylenedioxy group;
$R^2$ represents a nitrile group, a carboxyl group or an alkoxycarbonyl residue with up to six carbon atoms;
$R^3$ is a straight-chained or branched alkyl group with up to four carbon atoms or an amino group; and
$R^4$ represents a straight-chained or branched alkyl group with up to four carbon atoms; or a pharmaceutically accepatable salt thereof.
2. A compound as claimed in claim 1, wherein
$R^1$ represents phenyl or phenyl subtituted in two or three position, by halogen, nitro, methyl, methoxy, difluoromethoxy, trifluoromethoxy, dimethylamino or diethylamino, methylthio or trifluoromethyl, or phenyl disubstituted, in 2,3 positions by methoxy or methylenedioxy, or in 2,3 or 2,6 positions by halogen atoms, which may be the same or different;

$R^2$ represents a nitrile group, a carboxyl group or an alkoxycarbonyl residue of the formula $$CO_2R^5 \quad (II)$$

in which $R^5$ represents methyl, ethyl, n-propyl, isopropyl, n-butyl, isobutyl or methoxyethyl;

$R^3$ represents a methyl or ethyl residue or an amino group;

$R^4$ represents a methyl, ethyl, n-propyl or isopropyl residue.

3. Methyl-(±)-7-amino-5,8-dihydro-4-isopropoxy-5-(2-methoxyphenyl)-pyrido-[2,3-d]pyrimidin-6-carboxylate.

4. A compound as claimed in claim 1 and being the methyl, the 2-methoxyethyl, or the isopropyl ester of 5,8-dihydro-4-isopropoxy-7-methyl-5-(3-nitrophenyl)-pyrido-[2,3-d]pyrimidine-6-carboxylic acid.

5. A compound as claimed in claim 1 and being the methyl or ethyl ester of 5,8-dihydro-4-isopropoxy-7-methyl-5-(2-trifluoromethylphenyl)-pyrido[2,3-d]pyrimidine-6-carboxylic acid.

6. A compound as claimed in claim 1 and being ethyl 7-amino-5,8-dihydro-4-isopropoxy-5-(2-methoxyphenyl)-pyrido[2,3-d]pyrimidine-6-carboxylate.

7. A compound as claimed in claim 1 and being the isopropyl ester of 5,8-dihydro-4-methoxy-7-methyl-5-(3-nitrophenyl)-pyrido[2,3-d]pyrimidine-6-carboxylic acid.

8. A pharmaceutical composition comprising a vasospasmolytically effective amount of a compound as claimed in claim 1 with a pharmaceutically acceptable carrier or diluent.

9. A method for treating vascular diseases caused by smooth muscle contraction from potassium depolarization induced by calcium which comprises administering to a host suffering therefrom a calcium antagonist effective amount of pharmaceutical composition as claimed in claim 8 in unit dosage form.

* * * * *